(12) United States Patent
Yen et al.

(10) Patent No.: US 10,103,339 B2
(45) Date of Patent: Oct. 16, 2018

(54) IRIDIUM COMPLEXES AND ORGANIC ELECTROLUMINESCENCE DEVICE USING THE SAME

(71) Applicants: Feng-Wen Yen, Taipei (TW); Cheng-Hao Chang, Miao-Li (TW)

(72) Inventors: Feng-Wen Yen, Taipei (TW); Cheng-Hao Chang, Miao-Li (TW)

(*) Notice: Subject to any disclaimer, the term of this patent is extended or adjusted under 35 U.S.C. 154(b) by 394 days.

(21) Appl. No.: 15/014,049

(22) Filed: Feb. 3, 2016

(65) Prior Publication Data

US 2016/0233442 A1    Aug. 11, 2016

Related U.S. Application Data

(60) Provisional application No. 62/114,596, filed on Feb. 11, 2015.

(51) Int. Cl.
| | | |
|---|---|---|
| *H01L 51/00* | (2006.01) |
| *C09K 11/06* | (2006.01) |
| *C09K 11/02* | (2006.01) |
| *C07F 15/00* | (2006.01) |
| *H01L 51/50* | (2006.01) |

(52) U.S. Cl.
CPC ...... *H01L 51/0085* (2013.01); *C07F 15/0013* (2013.01); *C07F 15/0033* (2013.01); *C09K 11/02* (2013.01); *C09K 11/06* (2013.01); *H01L 51/0056* (2013.01); *H01L 51/0067* (2013.01); *H01L 51/0072* (2013.01); *H01L 51/0073* (2013.01); *H01L 51/0074* (2013.01); *H01L 51/0094* (2013.01); *C09K 2211/1007* (2013.01); *C09K 2211/1011* (2013.01); *C09K 2211/1029* (2013.01); *C09K 2211/1059* (2013.01); *C09K 2211/185* (2013.01); *H01L 51/5016* (2013.01); *H01L 2251/5384* (2013.01)

(58) Field of Classification Search
CPC ............ H01L 51/0085; H01L 51/0074; H01L 51/0094; H01L 51/0073; H01L 51/0056; H01L 51/0067; H01L 51/0072; H01L 51/5016; H01L 2251/5384; C07F 15/0013; C07F 15/0033; C09K 11/06; C09K 11/02; C09K 2211/1011; C09K 2211/1059; C09K 2211/185; C09K 2211/1007; C09K 2211/1029

See application file for complete search history.

(56) References Cited

U.S. PATENT DOCUMENTS

| 8,709,615 B2 | 4/2014 | Kottas et al. |
| 8,722,205 B2 | 5/2014 | Xia et al. |
| 8,778,508 B2 | 6/2014 | Kwong et al. |
| 8,779,176 B2 | 7/2014 | Anemian et al. |
| 8,795,850 B2 | 8/2014 | Kottas et al. |

(Continued)

*Primary Examiner* — Jeffrey T Barton
*Assistant Examiner* — Michael Y Sun

(57) ABSTRACT

The present invention discloses an iridium complexes and the organic EL device employing the iridium complexes as light emitting guest of emitting layer can display good performance like as lower driving voltage and power consumption, increasing efficiency and half-life time. Additional, the present invention provide the suitable emitting host (H1 to H6) to collocate with the energy level of iridium complexes for the present invention. Also provided a novel preparation method to synthesize the novel ligand such as 6-bromo-3,3-dimethyl-1-phenyl-1,3-dihydroindeno[2,1-b]carbazole.

10 Claims, 1 Drawing Sheet

| 14 | — metal electrode |
| 13 | — electron injection layer |
| 12 | — electron transport layer |
| 11 | — hole blocking layer |
| 10 | — emitting layer |
| 9 | — electron blocking layer |
| 8 | — hole transport layer |
| 7 | — hole injection layer |
| 6 | — transparent electrode |

(56) References Cited

U.S. PATENT DOCUMENTS

| | | | |
|---|---|---|---|
| 2003/0068535 A1* | 4/2003 | Takiguchi | C07F 15/0033 428/704 |
| 2010/0244004 A1* | 9/2010 | Xia | C07F 15/0033 257/40 |
| 2012/0061654 A1* | 3/2012 | Rayabarapu | C07F 15/0033 257/40 |

* cited by examiner

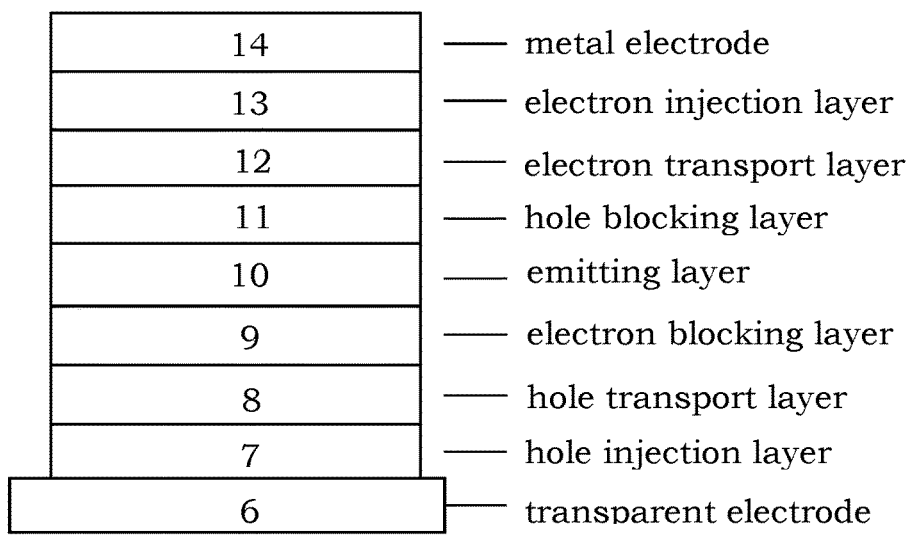

IRIDIUM COMPLEXES AND ORGANIC ELECTROLUMINESCENCE DEVICE USING THE SAME

This application claims benefit of provisional of U.S. Patent Ser. No. 62/114,596, filed Feb. 11, 2015.

FIELD OF INVENTION

The present invention generally relates to a iridium complexes and organic electroluminescence (herein referred to as organic EL) device using the iridium complexes. More specifically, the present invention relates to the iridium complexes having general formula (1), an organic EL device employing the iridium complexes as phosphorescent guest material of emitting layer.

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML) and an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

For full-colored flat panel displays in AMOLED or OLED lighting panel the material used for the phosphorescent guest for emitting layer are still unsatisfactory in half-lifetime, efficiency and driving voltage. These metallic complexes still have disadvantages for industrial practice use.

In the present invention, for the purpose to prolong the half-life time and lower driving voltage for phosphorescent guest in emitting layer for organic EL device, we employ an pyridine-substituted fused fluorene derivative skeleton link to iridium metal, then chelate with one or two 2-phenylpyridine group to finish the metallic complexes represented as general formula (1). The iridium complexes show good thermal stability and charge carrier mobility for organic EL device. Some prior-arts of iridium complexes such as U.S. Pat. No. 8,795,850B2, U.S. Pat. No. 8,778,508B2, U.S. Pat. No. 8,722,205B2, U.S. Pat. No. 8,709,615B2. U.S. Pat. No. 8,779,176B2. But there are no prior arts demonstrate a pyridine-substituted fused fluorene derivative skeleton link to iridium complexes used as phosphorescent emitting guest for organic EL device.

SUMMARY OF THE INVENTION

According to the reasons described above, the present invention has the objective of resolving such problems of the prior-art and offering a light emitting device which is excellent in its thermal stability, high luminance efficiency and long half-life time. The present invention disclose a novel iridium complexes having general formula (1), used as a phosphorescent emitting guest have good charge carrier mobility and excellent operational durability can lower driving voltage and power consumption, increasing efficiency and half-life time of organic EL.

The present invention has the economic advantages for industrial practice. Accordingly, the present invention discloses the iridium complexes which can be used for organic EL device is disclosed. The mentioned the iridium complexes is represented by the following formula (1):

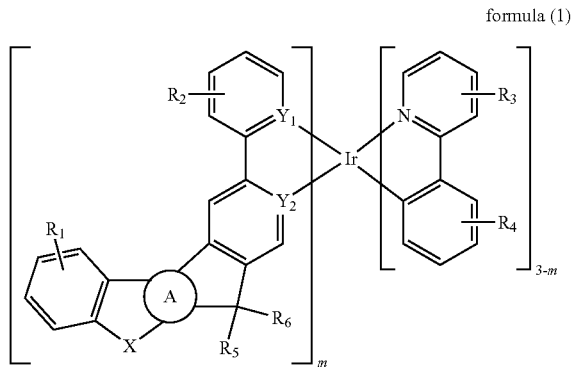

formula (1)

wherein m represents an integer of 1 or 2, X independently represents a divalent bridge selected from the atom or group consisting from O, S and N($R_7$), A ring represents a substituted or unsubstituted benzene ring, $Y_1$ and $Y_2$ are different and $Y_1$, $Y_2$ represent nitrogen or carbon atom; $R_1$ to $R_7$ are the same or different, $R_1$ to $R_7$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

BRIEF DESCRIPTION OF THE DRAWINGS

FIG. 1 show one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is hole blocking layer which is deposited onto 10, 12 is electron transport layer which is deposited onto 11, and 13 is electron injection layer which is deposited onto 12.

DESCRIPTION OF THE PREFERRED EMBODIMENTS

What probed into the invention is the iridium complexes and organic EL device using the iridium complexes. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, iridium complexes which can be used as phosphorescent guest material of emitting layer for organic EL device are disclosed. The mentioned iridium complexes is represented by the following formula (1):

formula (1)

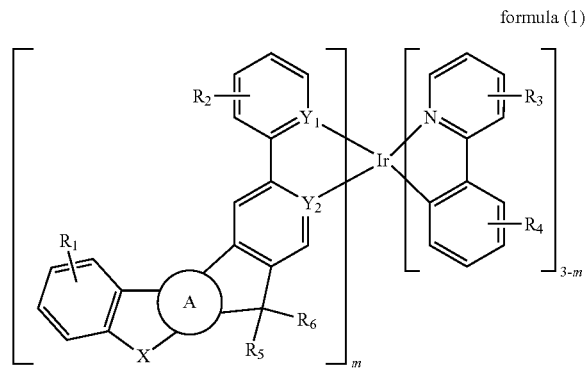

wherein m represents an integer of 1 or 2, X independently represents a divalent bridge selected from the atom or group consisting from O, S and N($R_7$), A ring represents a substituted or unsubstituted benzene ring, $Y_1$ and $Y_2$ are different and $Y_1$, $Y_2$ represent nitrogen or carbon atom; $R_1$ to $R_7$ are the same or different, $R_1$ to $R_7$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

The iridium complexes according to the above-mentioned formula (1), wherein the iridium complexes is represented as the following formula (2):

formula (2)

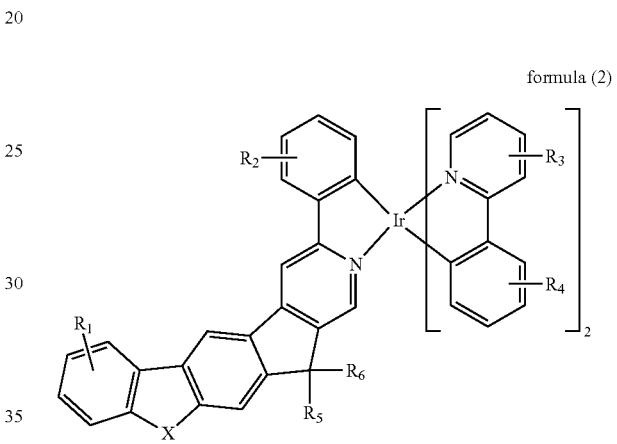

in the above-mention formula (2), wherein X and $R_1$ to $R_6$, each is the same as the described in the formula (1).

The iridium complexes according to the above-mentioned formula (1), wherein the iridium complexes are represented as the following formula (3):

formula (3)

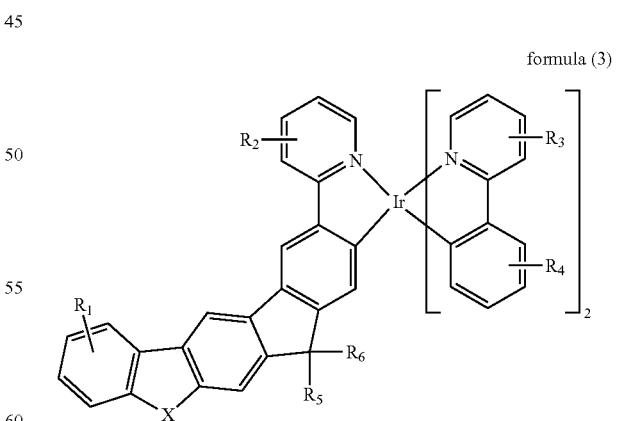

in the above-mention formula (3), wherein X and $R_1$ to $R_6$, each is the same as the described in the formula (1).

The iridium complexes according to the above-mentioned formula (1), wherein the iridium complexes are represented as the following formula (4):

formula (4)

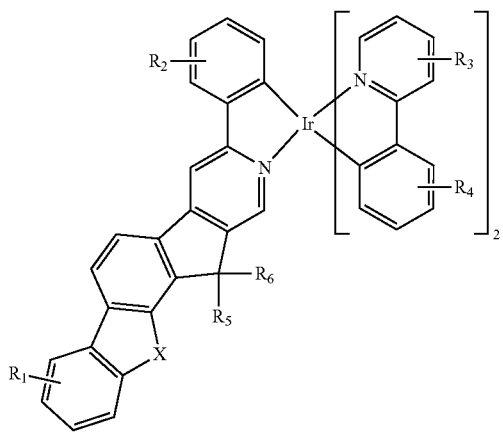

in the above-mention formula (4), wherein X and $R_1$ to $R_6$, each is the same as the described in the formula (1).

The iridium complexes according to the above-mentioned formula (1), wherein the iridium complexes are represented as the following formula (5):

formula (5)

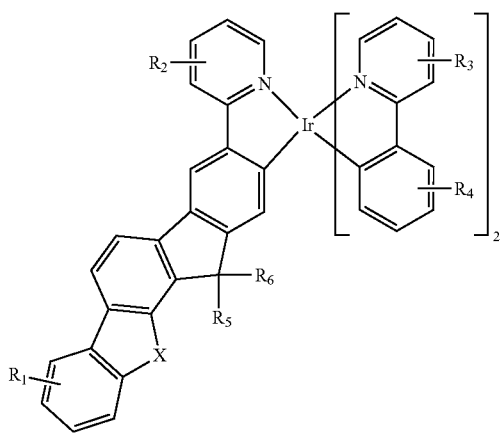

in the above-mention formula (5), wherein X and $R_1$ to $R_6$, each is the same as the described in the formula (1).

The iridium complexes according to the above-mentioned formula (1), wherein the iridium complexes are represented as the following formula (6):

formula (6)

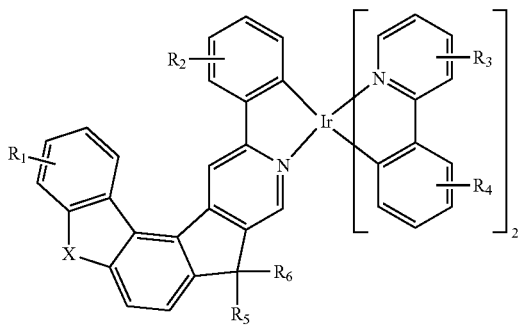

in the above-mention formula (6), wherein X and $R_1$ to $R_6$, each is the same as the described in the formula (1).

The iridium complexes according to the above-mentioned formula (1), wherein the iridium complexes are represented as the following formula (7):

formula (7)

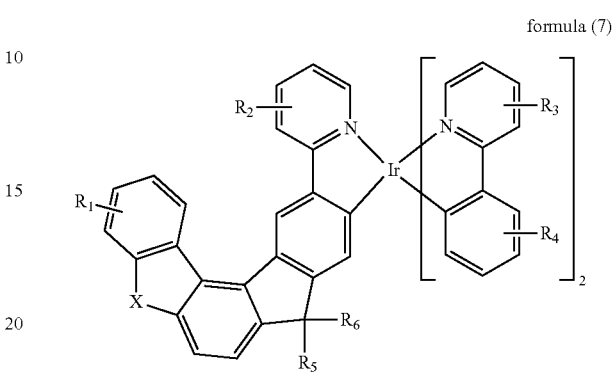

in the above-mention formula (7), wherein X and $R_1$ to $R_6$, each is the same as the described in the formula (1).

In this embodiment, some specific iridium complexes are shown below:

Ex1

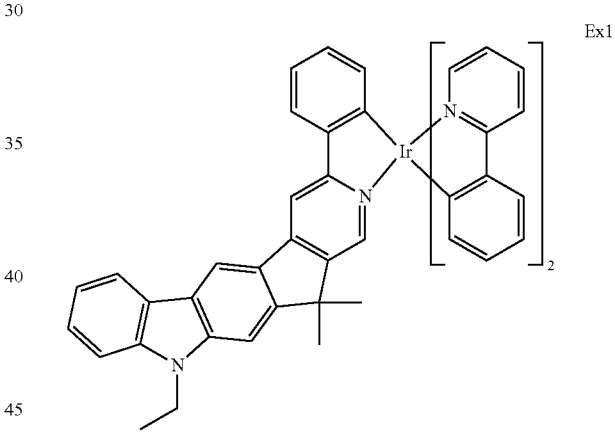

Ex2

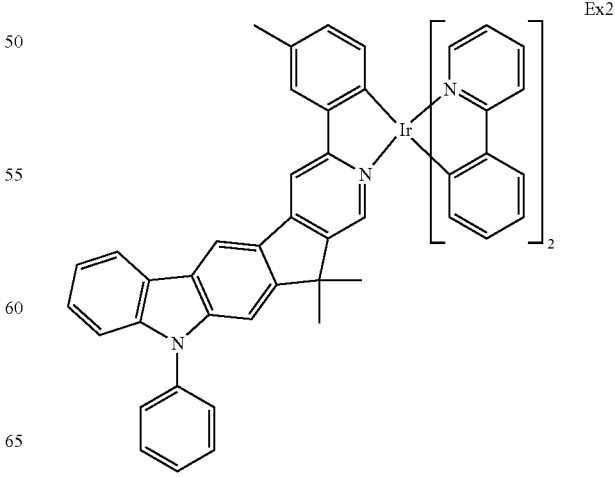

Ex3
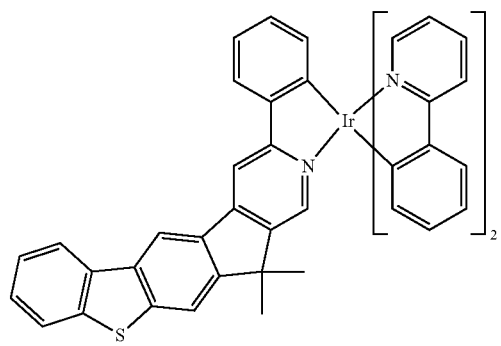
Ex4
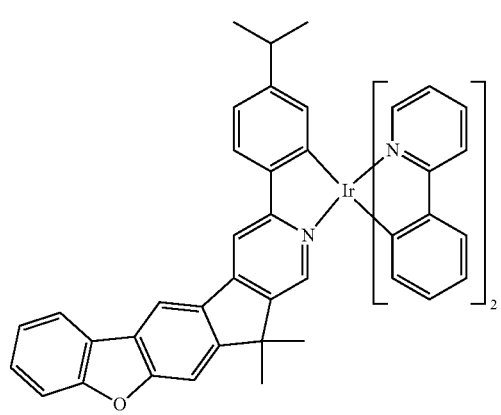
Ex5
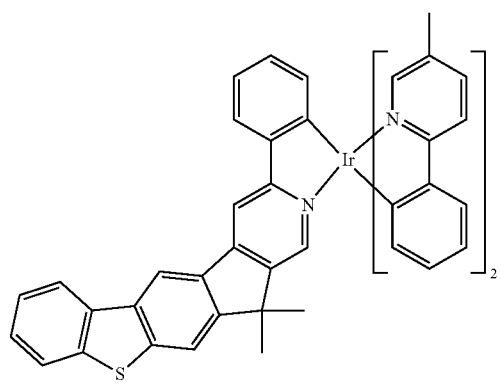
Ex6
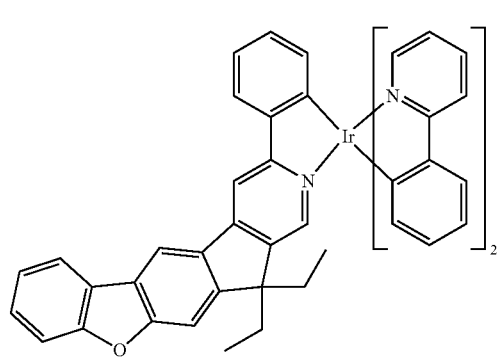
Ex7
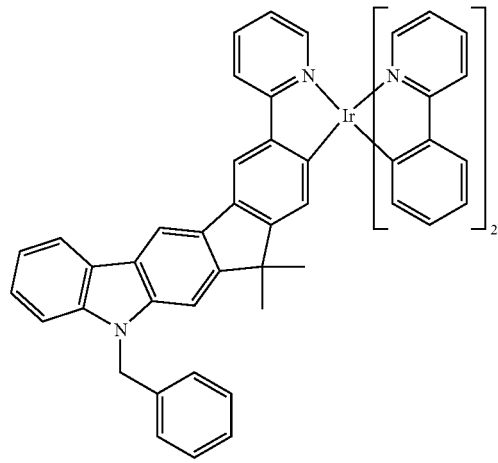
Ex8
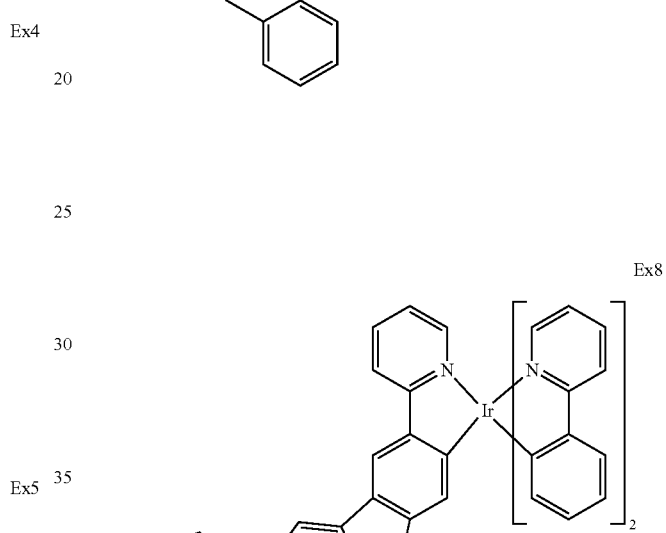
Ex9
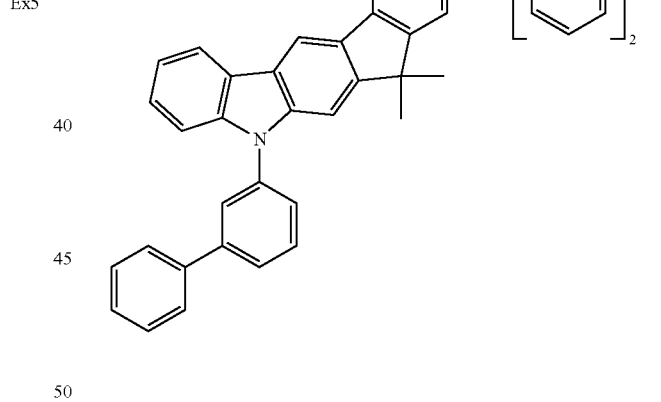

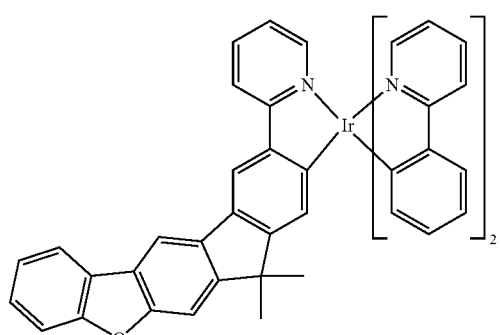
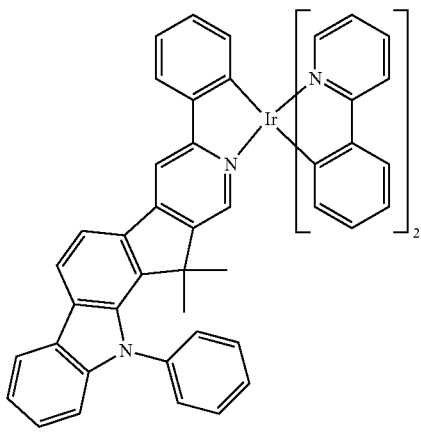
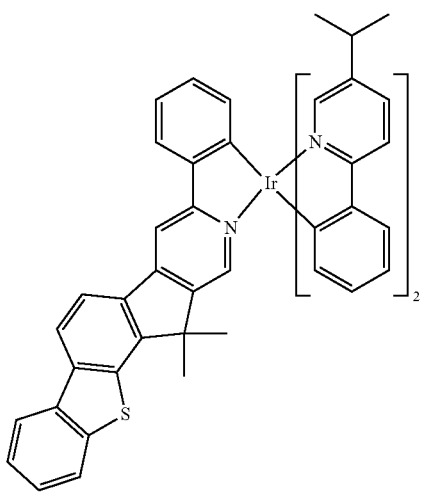
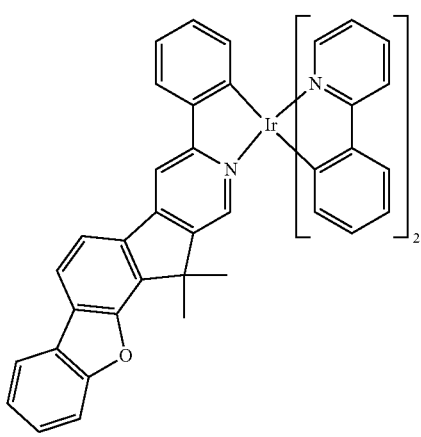

Ex17
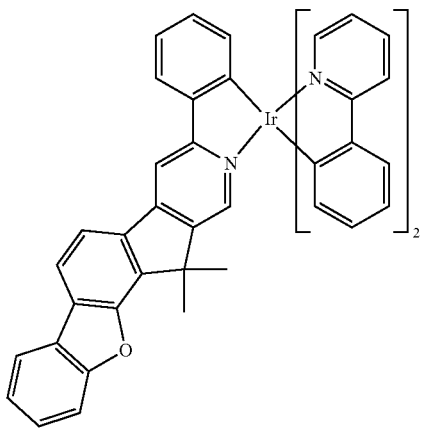
Ex18
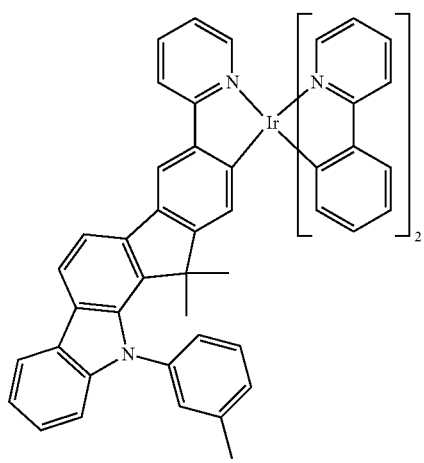
Ex19
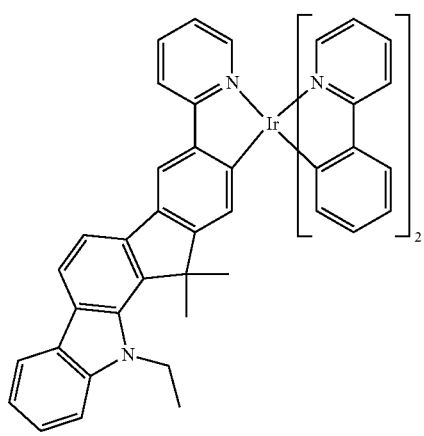
Ex20
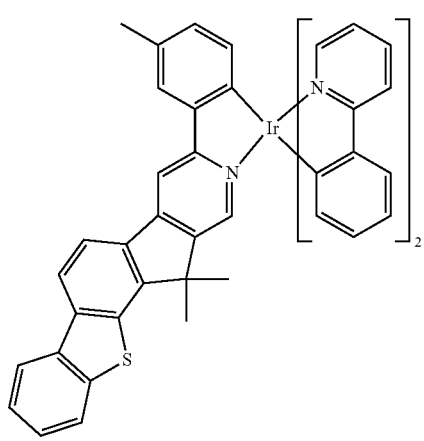
Ex21
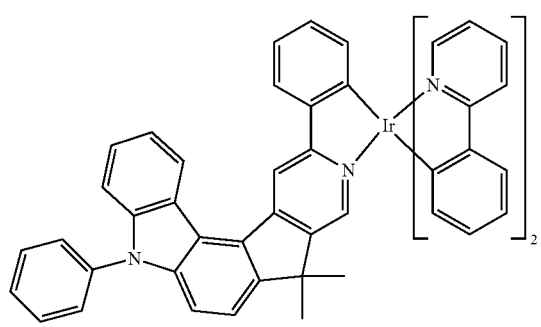
Ex22
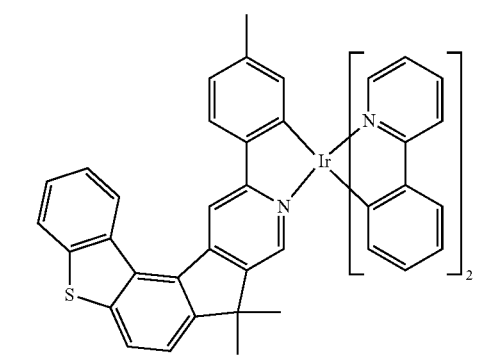
Ex23
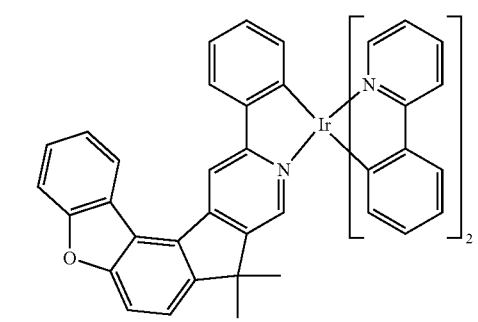

Ex24

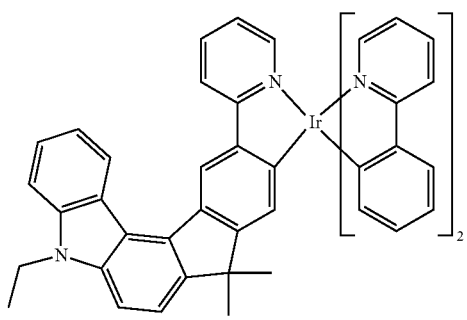

Ex25

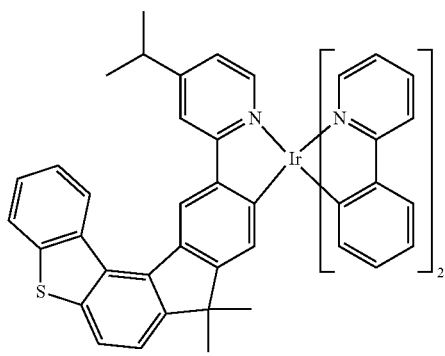

Ex26

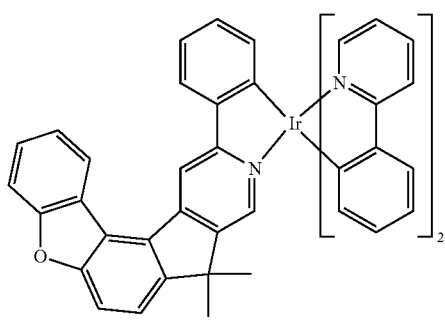

Detailed preparation for the iridium complexes in the present invention could be clarified by exemplary embodiments, but the present invention is not limited to exemplary embodiments. EXAMPLE 1 show the preparation for examples of the derivative in the present invention. EXAMPLE 2 shows the fabrication of organic EL device and I-V-B, half-life time of organic EL device testing report.

EXAMPLE 1

Synthesis of EX11

Synthesis of 3-bromo-9,9-dimethyl-6-(2-nitrophenyl)-9H-fluorene

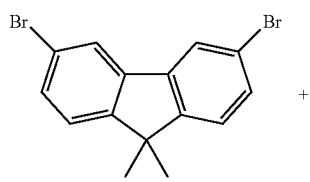
+

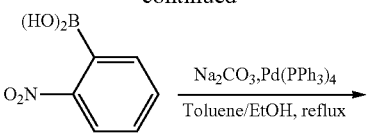

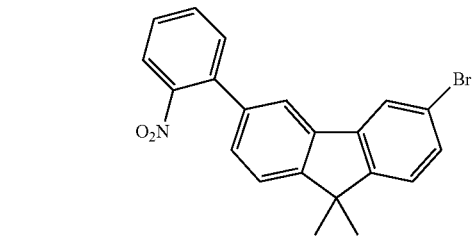

A mixture of 35.2 g (100 mmol) of 3,6-dibromo-9,9-dimethyl-9H-fluorene, 18.4 g (110 mmol) of 2-nitrophenylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 100° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica gel to give product (30.7 g, 78.0 mmol, 78%) as a white solid.

Synthesis of 6-bromo-3,3-dimethyl-1,3-dihydroindeno[2,1-b] carbazole

A mixture of 30.7 g (78 mmol) of 3-bromo-9,9-dimethyl-6-(2-nitrophenyl)-9H-fluorene, 200 ml of triethylphosphite, 100 ml of 1,2-dichlorobenzene, was placed under nitrogen, and then heated at 160° C. overnight. After finishing the reaction, the mixture was allowed to cool to room temperature. Than 1200 ml of MeOH was added, while stirring and the precipitated product was filtered off with suction. To give 7.9 g (yield 28%) of yellow product which was purified by column chromatography on silica gel (Hx-CH$_2$Cl$_2$).

Synthesis of 6-bromo-3,3-dimethyl-1-phenyl-1,3-dihydro indeno[2,1-b]carbazole

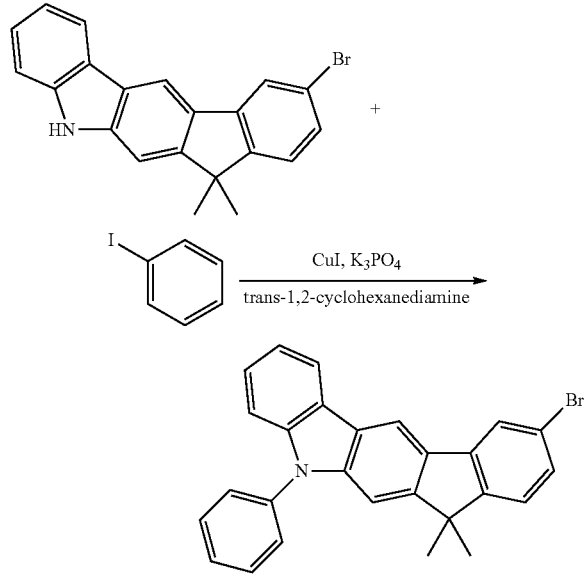

A mixture of 7.9 g (21.8 mmole) 6-bromo-3,3-dimethyl-1,3-dihydroindeno[2,1-b]carbazole, 4.9 g (24 mmole) of iodobenzene, 17.1 g (90 mmole) of copper(I)iodide, 18.9 g (90 mmole) of potassium phosphate, 10.2 g (90 mmole) of trans-1,2-cyclohexanediamine and 1,4-dioxane 300 ml were refluxed under nitrogen for about overnight. Then, the solution was filtered at 110° C. To receive the filtrate, And the 1,4-dioxane was removed under reduced pressure from the filtrate. The filtrate was extracted with 200 ml dichloromethane and 400 ml of water, the organic layer was dried with anhydrous magnesium sulfate, the solvent was removed and the residue was purified by column chromatography on silica gel (hexane-ethyl acetate) to give product 6.8 g (71%). 1NMR(CDCl3, 400 MHz): chemical shift (ppm) 8.56~8.23 (m, 3H), 7.91~8.81 (m, 2H), 7.77~7.75 (m, 4H), 7.52~7.28 (m, 5H), 1.66 (s, 6H).

Synthesis of 3,3-dimethyl-1-phenyl-6-(pyridin-2-yl)-1,3-dihydroindeno[2,1-b]carbazole

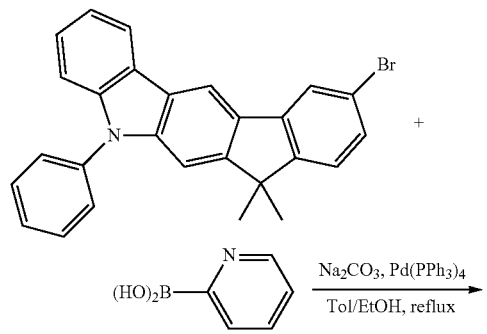

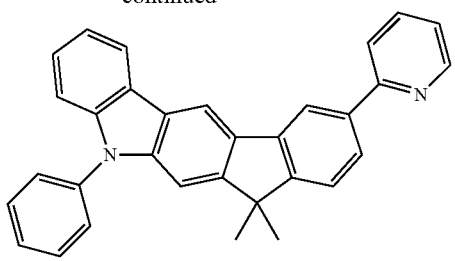

A mixture of 6.8 g (15.5 mmol) of 6-bromo-3,3-dimethyl-1-phenyl-1,3-dihydroindeno[2,1-b]carbazole, 3.3 g (21 mmol) of pyridin-2-ylboronic acid, 0.44 g (0.4 mmol) of tetrakis(triphenylphosphine) palladium, 30 ml of 2M Na$_2$CO$_3$, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica (Hx~EA) to give product 5.3 g (78%).

Synthesis of Dichloro-Bridged Dimer

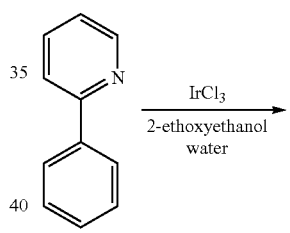

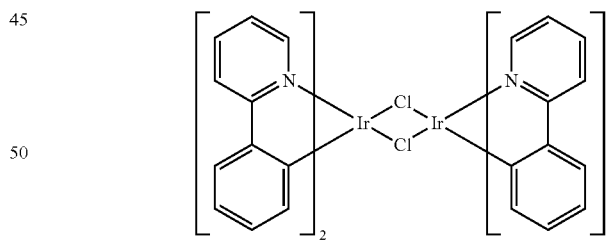

A mixture of 7.35 g (20 mmol) of iridium(III)chloride, 13 g (85 mmol) of 2-phenylpyridine, 120 ml of 2-methoxyethanol and 30 ml of distilled water, was placed under nitrogen, and then heated reflux overnight. After finishing the reaction, the mixture was allowed to cool to room temperature. The yellow precipitate formed was vacuum filtered and washed with ethanol and hexanes. The dichloro-bridged dimer was dried in a vacuum oven to give 1.0 g. The product was not purified any further but used directly in the next step.

Synthesis of Iridium Triflate Precursor

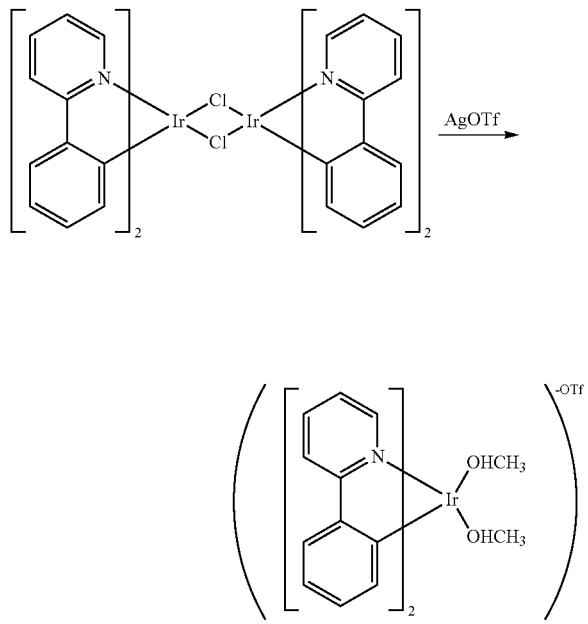

A mixture of 9.6 g of dichloro-bridged dimer, 4.6 g (17.5 mmol) of silver triflate, 300 ml of dichloromethane and 5 ml of methanol, was placed under nitrogen, and then stirred overnight. After finishing the reaction, the silver chloride was filtered off. The solvent was evaporated. 10.6 g of product was obtained. The product was not purified any further but used directly in the next step.

Synthesis of Example 11

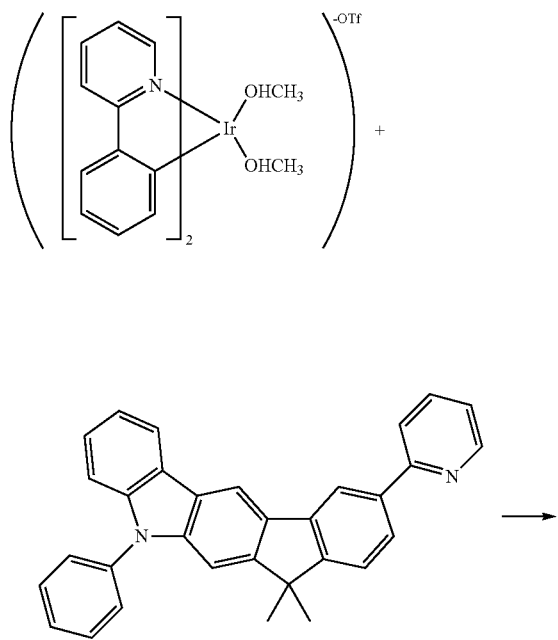

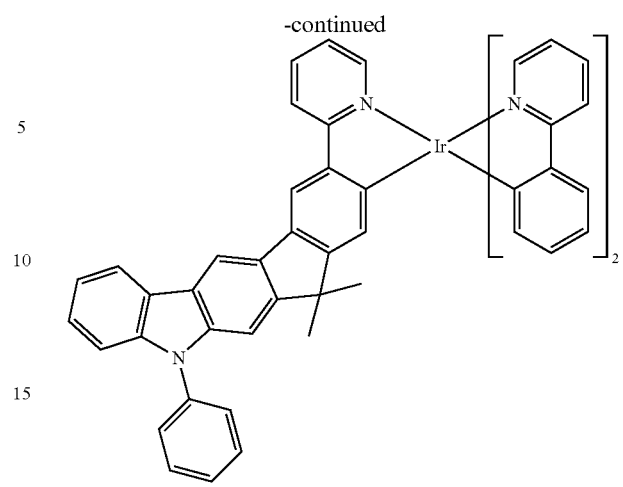

A mixture of 4.7 g (6 mmol) of iridium triflate precursor, 5.3 g (12.1 mmol) of 3,3-dimethyl-1-phenyl-6-(pyridin-2-yl)-1,3-dihydroindeno[2,1-b]carbazole, 60 ml of EtOH and 15 ml of MeOH, was placed under nitrogen, and then heated reflux overnight. After finishing the reaction, the mixture was allowed to cool to room temperature. The yellow precipitate formed was vacuum filtered and washed with ethanol and hexanes, the product was purified by vacuum sublimation to give 2.1 g of yellow product. MS (m/z, FAB+): 936.4; 1H NMR (CDCl$_3$, 500 MHz): chemical shift (ppm) 8.93 (s, 1H), 8.64~8.61 (m, 5H), 8.17~7.9 (m, 4H), 7.83~7.50 (m, 13H), 7.44~7.15 (m, 8H), 6.94~6.89 (m, 2H), 1.65 (s, 6H).

GENERAL METHOD OF PRODUCING ORGANIC EL DEVICE

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 1000).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f: 2,3-]quinoxaline-2,3,6,7,10,11-hexacarbonitrile (HAT-CN) is used as hole injection layer in this organic EL device, and N,N-Bis (naphthalene-1-yl)-N,N-bis (phenyl)-benzidine (NPB) is most widely used as the hole transporting layer, N-(biphenyl-4-yl)-9,9-dimethyl-N-(4'-phenylbiphenyl-4-yl)-9H-fluoren-2-amine (EB2) is used as electron blocking layer, and the chemical structure shown below:

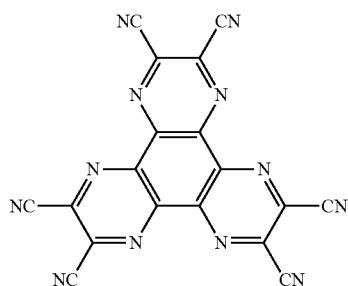

HAT-CN

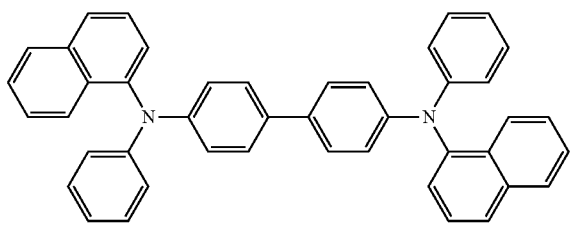

NPB

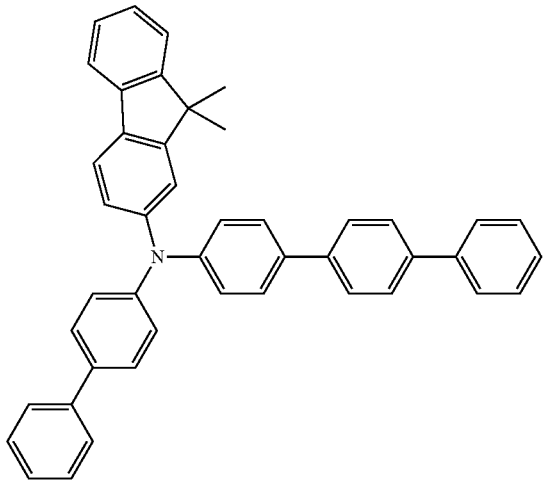

EB2

In the present invention the phosphorescent emitting host used as the following formulas:

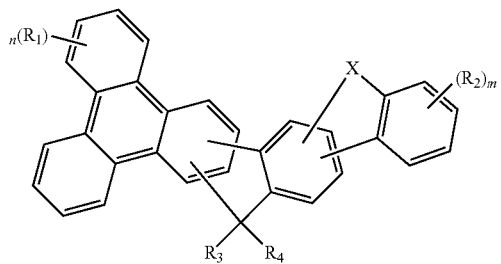

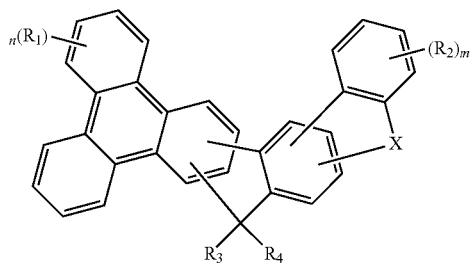

wherein X is a divalent bridge selected from the atom or group consisting from O, S, $C(R_8)_2$, $N(R_9)$ and $Si(R_{10})_2$, m represents an integer of 0 to 4, n represents an integer of 0 to 8, $R_1$ to $R_4$ and $R_8$ to $R_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms; wherein the preferably phosphorescent light emitting host is selected from the group consisting of:

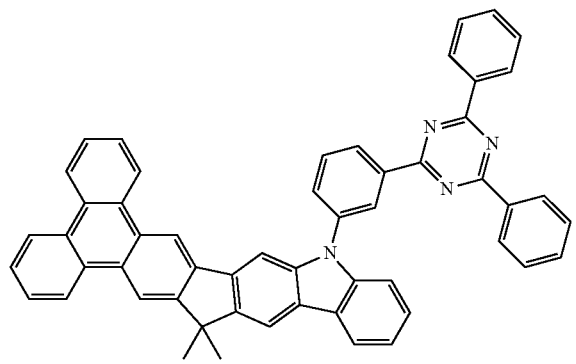

H1

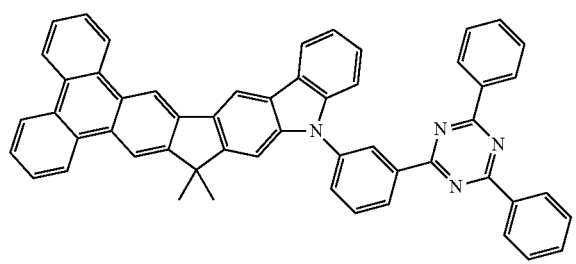

H2

H3

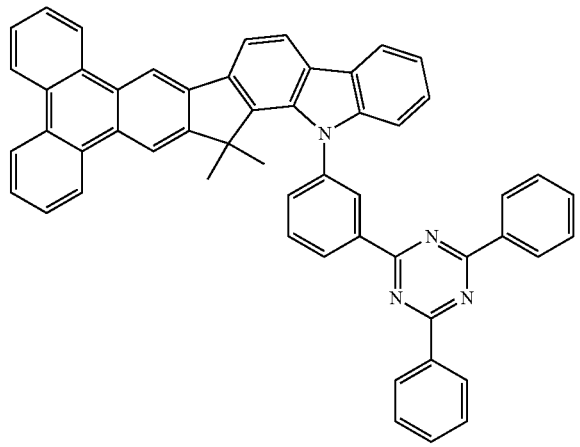

H4

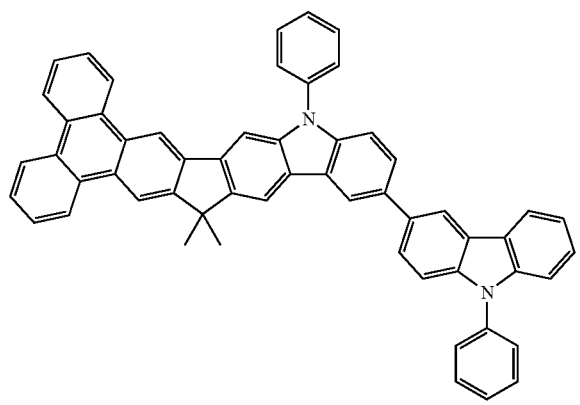

H5

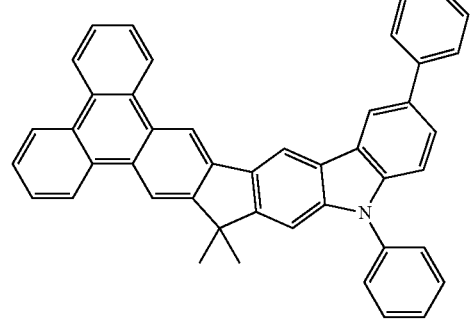

H6

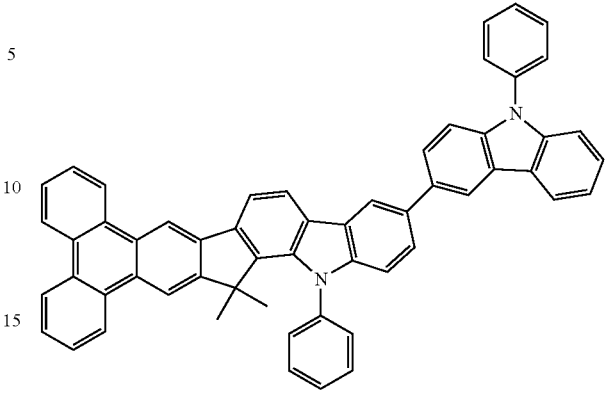

Organic iridium complexes are widely used as phosphorescent guest for light emitting layer, Ir(ppy)₃ is widely used for phosphorescent green guest of light emitting layer for comparable materials in the present invention.

Ir(ppy)3

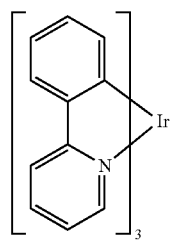

HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

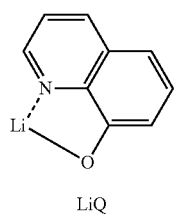

LiQ

ET2

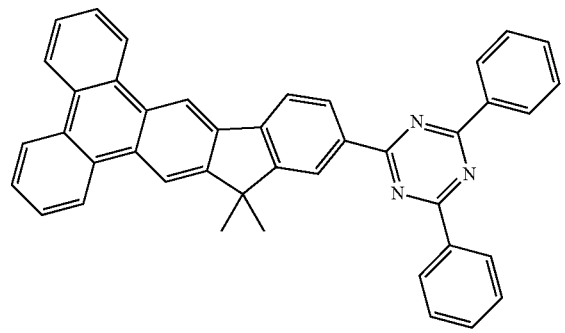

-continued

HB3

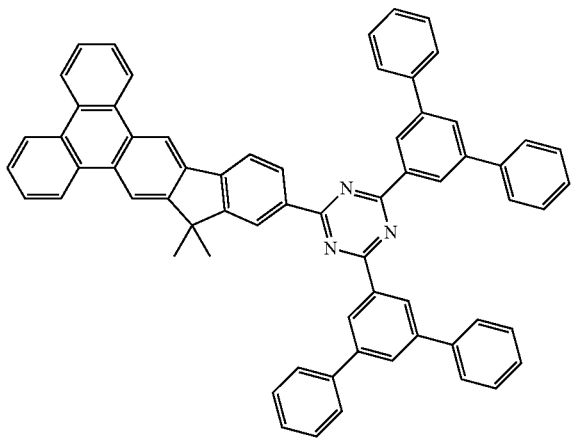

Ex11

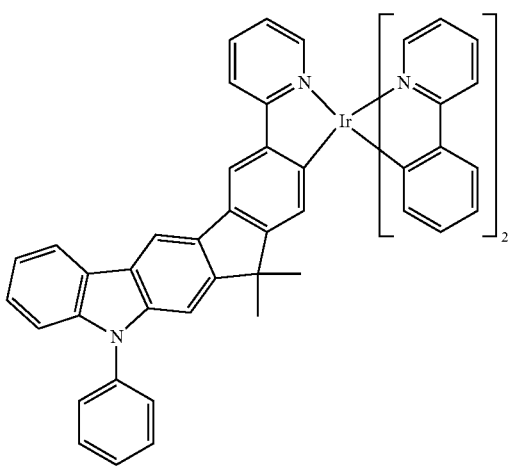

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 2

Using a procedure analogous to the above mentioned general method, phosphorescent emitting organic EL device having the following device structure was produced (See FIG. 1). Device: ITO/HAT-CN(20 nm)/NPB (110 nm)/EB2(5 nm)/Emitting host doped 12% phosphorescent emitting guest (30 nm)/HB3(10 nm)/ET2 doped 40% LiQ (35 nm)/LiQ (1 nm)/Al (160 nm). The I-V-B (at 1000 nits) and half-life time of phosphorescent emitting organic EL device testing report as Table 1. The half-life time is defined that the initial luminance of 1000 $cd/m^2$ has dropped to half.

TABLE 1

| Emitting host | Emitting guest | Voltage (V) | Efficiency (cd/A) | Color | Half-life time (hour) |
|---|---|---|---|---|---|
| H1 | EX11 | 3.6 | 45 | green | 1380 |
| H2 | Ir(ppy)₃ | 4.1 | 44 | green | 960 |
| H2 | EX11 | 3.3 | 48 | green | 1250 |
| H3 | EX11 | 3.6 | 42 | green | 1150 |
| H4 | EX11 | 3.8 | 28 | green | 1100 |
| H5 | EX11 | 4.0 | 21 | green | 1050 |
| H6 | EX11 | 3.8 | 25 | green | 1010 |
| H2 + H6 | Ir(ppy)₃ | 3.5 | 54 | green | 1120 |
| H2 + H6 | EX11 | 3.2 | 56 | green | 1580 |

In the above preferred embodiments for phosphorescent organic EL device test report (see Table 1), we show that the iridium complexes with a general formula (1) used as light emitting guest of emitting layer for organic EL device in the present invention display good performance than the prior art of organic EL materials. More specifically, the organic EL device in the present invention use the iridium complexes with a general formula (1) as light emitting guest material to collocate with emitting host material H1 to H6 shown lower power consumption, longer half-life time and higher efficiency.

To sum up, the present invention discloses an iridium complexes which can be used as light emitting guest of emitting layer for organic EL device are disclosed. The mentioned the iridium complexes represented by the following formula (1):

formula (1)

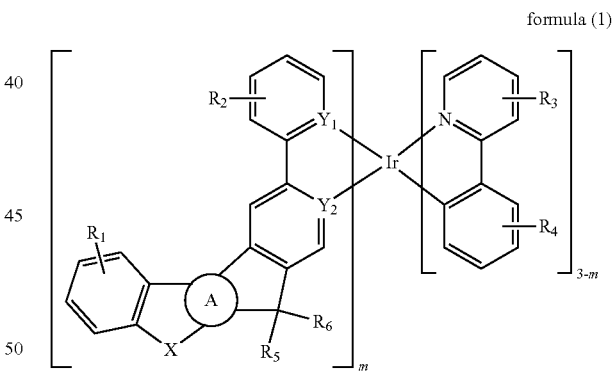

wherein m represents an integer of 1 or 2, X independently represents a divalent bridge selected from the atom or group consisting from O, S and N(R₇), A ring represents a substituted or unsubstituted benzene ring, Y₁ and Y₂ are different and Y₁, Y₂ represent nitrogen or carbon atom; R₁ to R₇ are the same or different, R₁ to R₇ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:
1. An iridium complex is represented by the following formula (1):

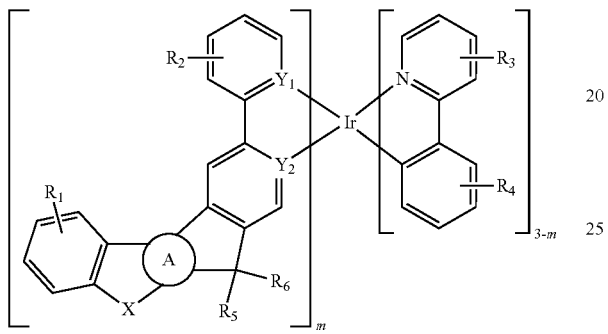

formula (1)

wherein m represents an integer of 1 or 2, X represents a divalent bridge selected from the group consisting of O, S and $N(R_7)$, A ring represents a substituted or unsubstituted benzene ring, $Y_1$ and $Y_2$ are different and $Y_1$, $Y_2$ represent nitrogen or carbon atom; $R_1$ to $R_7$ are the same or different, $R_1$ to $R_7$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

2. The iridium complex according to claim 1, wherein the iridium complex formula (1) is represented by the following formula (2) to formula (7):

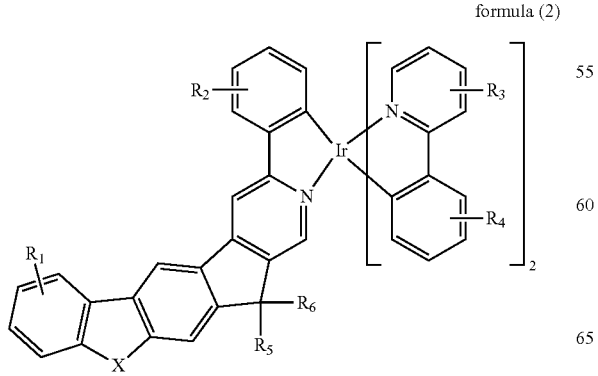

formula (2)

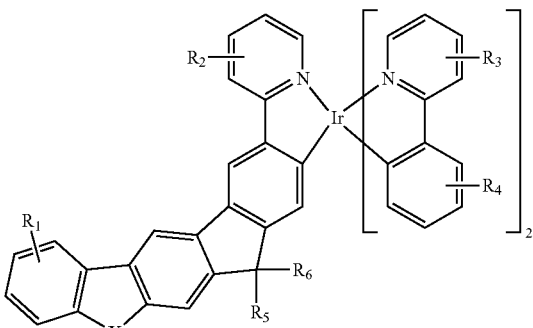

formula (3)

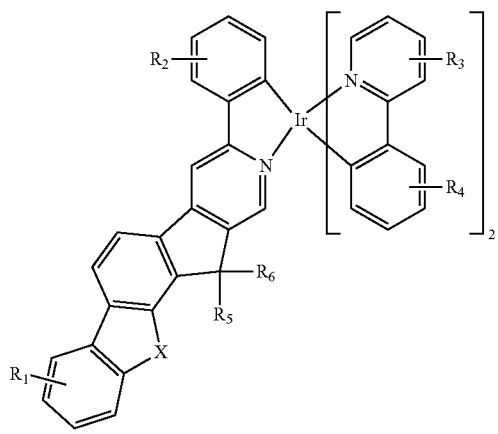

formula (4)

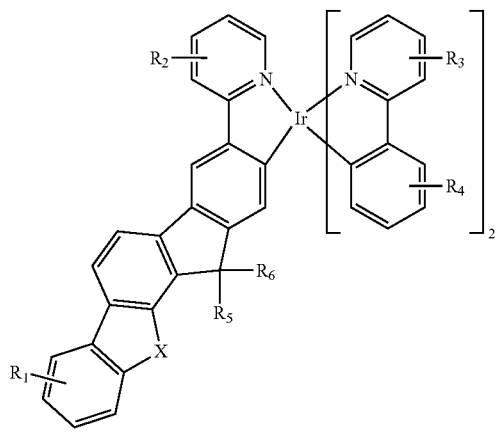

formula (5)

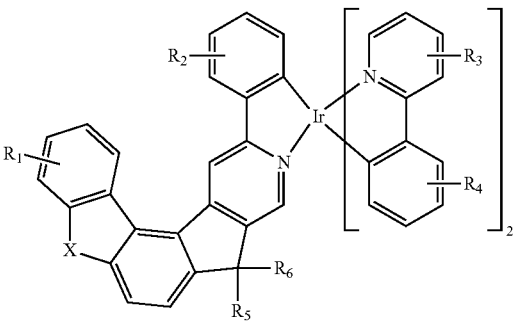

formula (6)

formula (7)

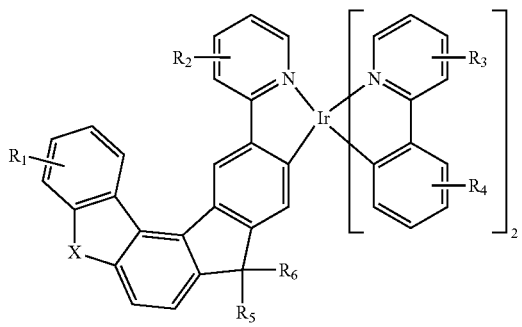

wherein X represents a divalent bridge selected from the group consisting of O, S and N(R$_7$), R$_1$ to R$_7$ are the same or different, R$_1$ to R$_7$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

3. An organic electroluminescence device comprising a pair of electrodes consisting of a cathode and an anode, and between the pairs of electrodes comprising at least a light emitting layer, one or more layers of organic thin film layer, wherein the light emitting layer comprising the iridium complex for an organic electroluminescence device according to claim 1.

4. The organic electroluminescence device according to claim 3, wherein the light emitting layer comprising the iridium complex with a general formula (1) is a phosphorescent guest material.

5. The organic electroluminescent device according to claim 3, wherein the light emitting layer comprising two or three types of emitting host with the following formulas:

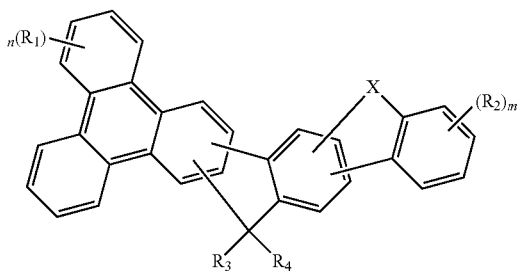

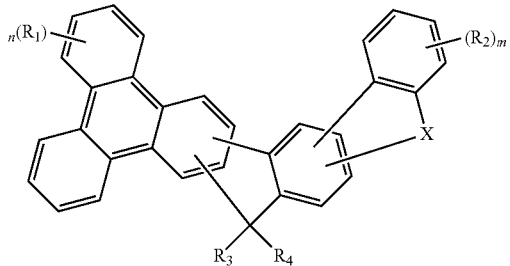

wherein X is a divalent bridge selected from the group consisting of O, S, C(R$_8$)$_2$, N(R$_9$) and Si(R$_{10}$)$_2$, m represents an integer of 0 to 4, n represents an integer of 0 to 8, R$_1$ to R$_4$ and R$_8$ to R$_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

6. The organic electroluminescent device according to claim 3, wherein the light emitting host is selected from the group consisting of:

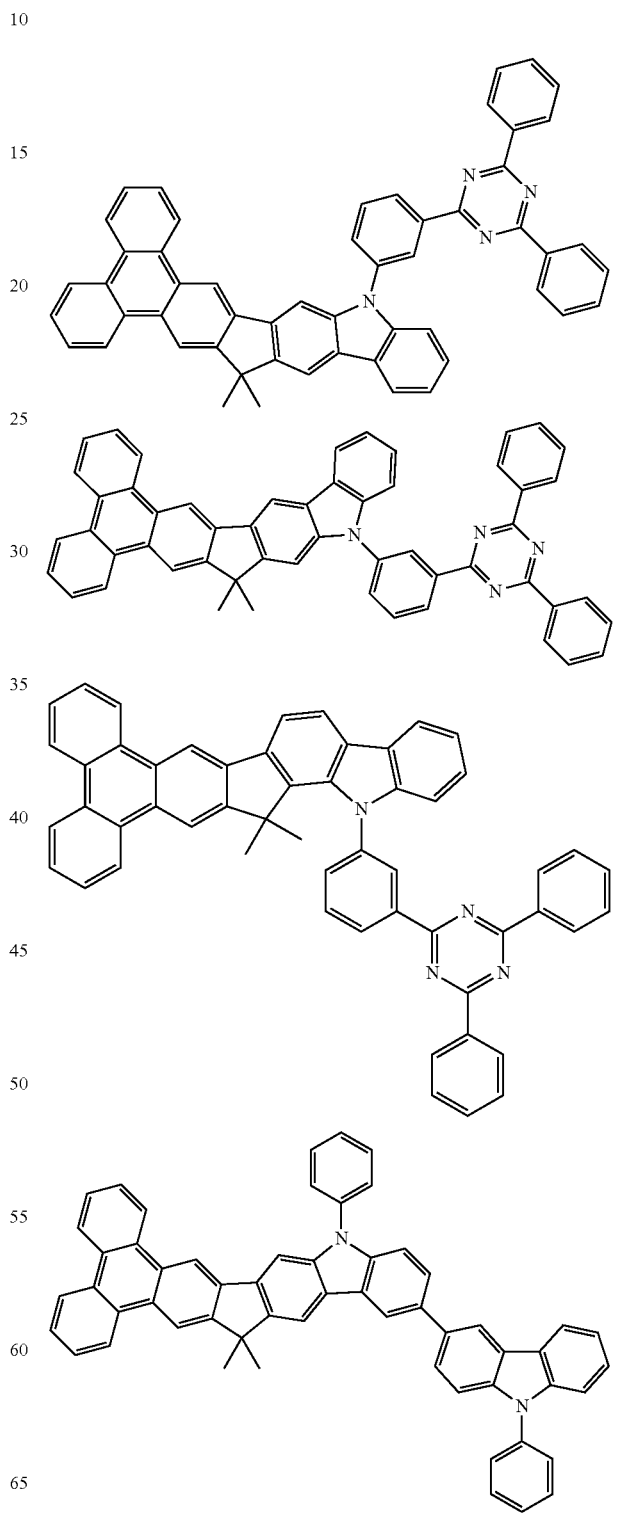

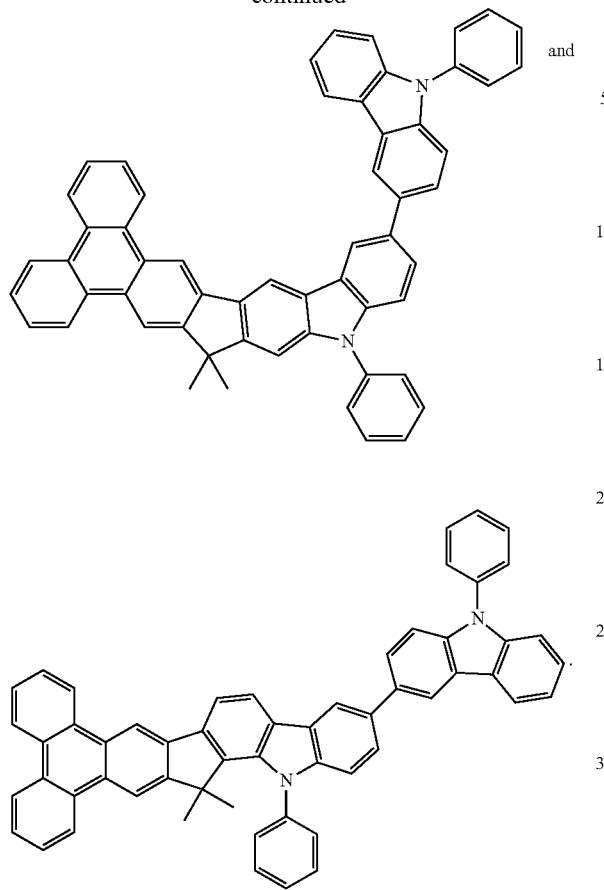

and

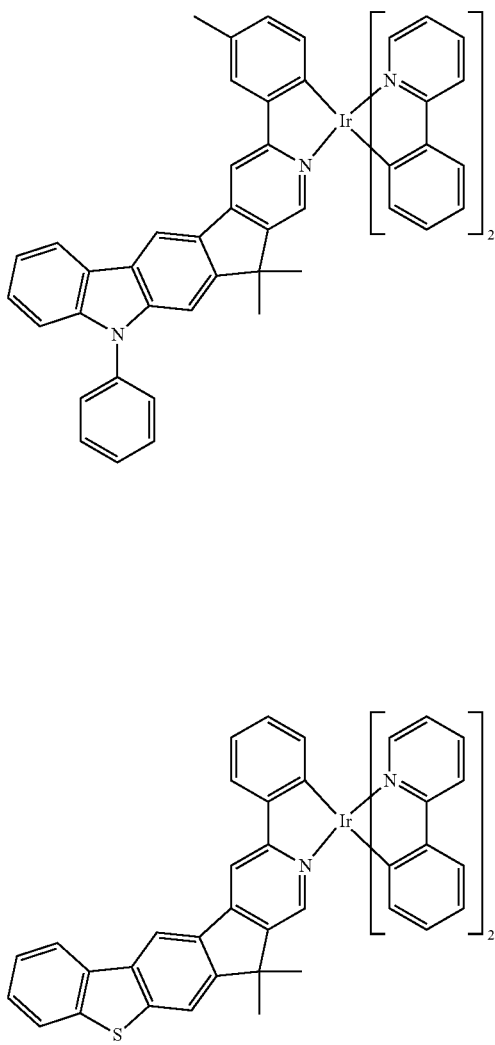

7. The organic electroluminescent device according to claim 3, wherein the light emitting layer emits phosphorescent green and yellow lights.

8. The organic electroluminescent device according to claim 3, wherein the device is an organic light emitting device.

9. The organic electroluminescent device according to claim 3, wherein the device is a lighting panel.

10. The iridium complex according to claim 1 with a general formula (1) is selected from the group consisting of:

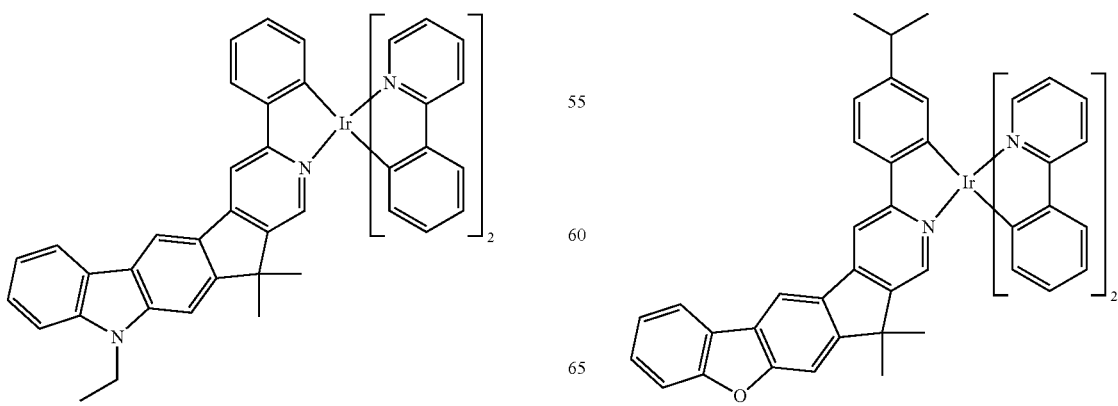

Ex5
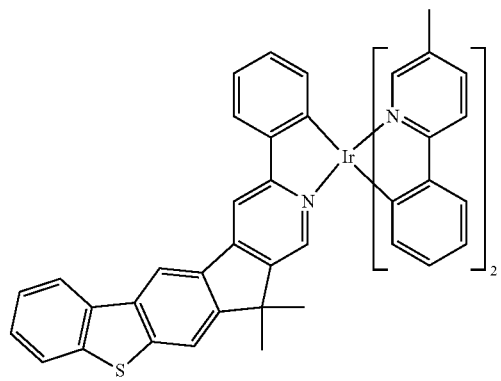
Ex6
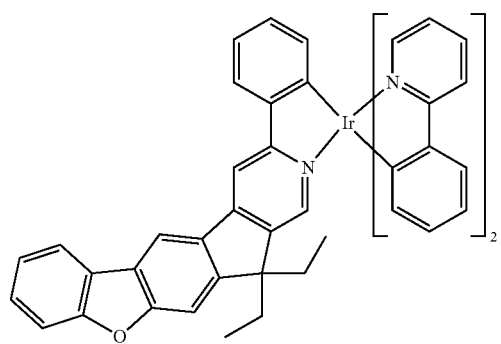
Ex7
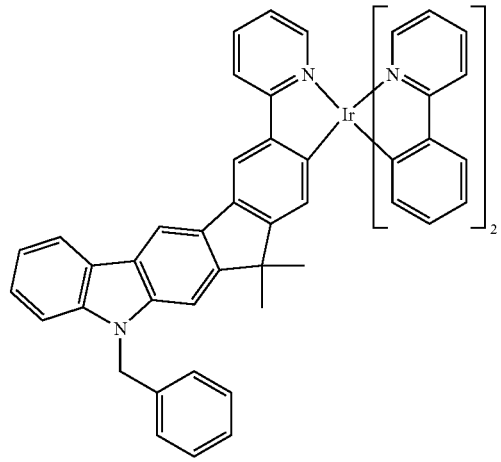
Ex8
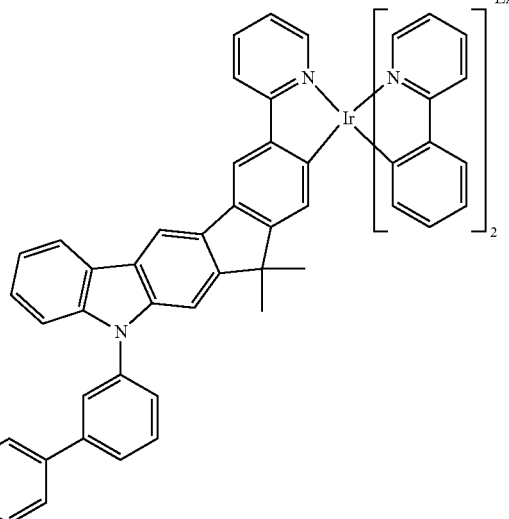
Ex9
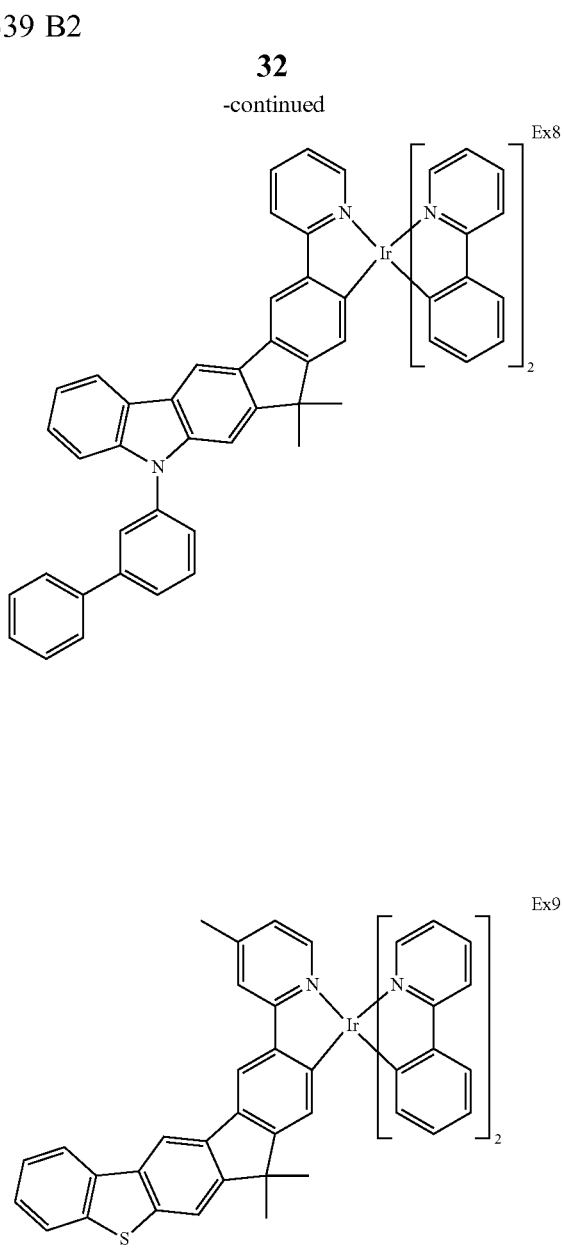
Ex10
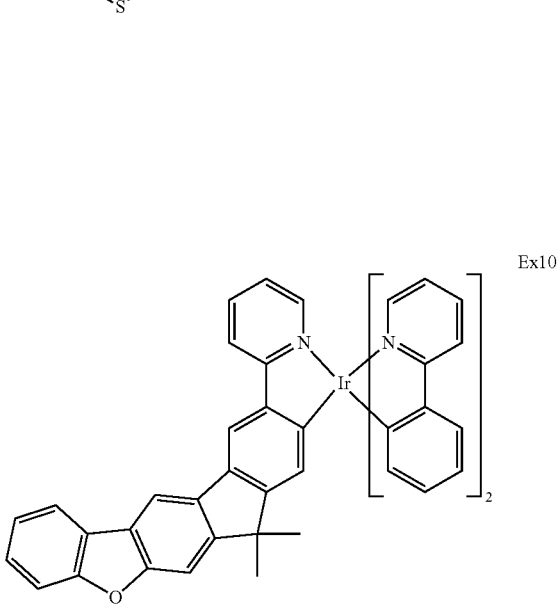

-continued
Ex11
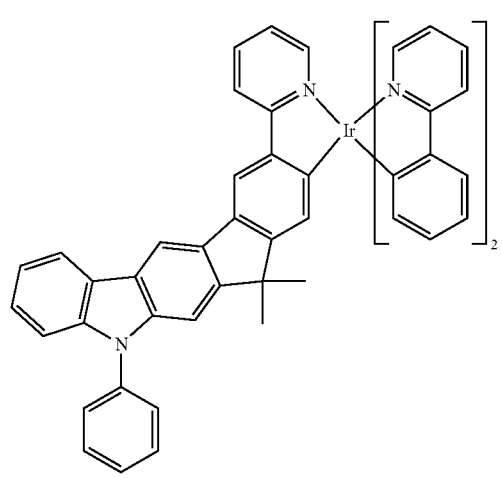
Ex12
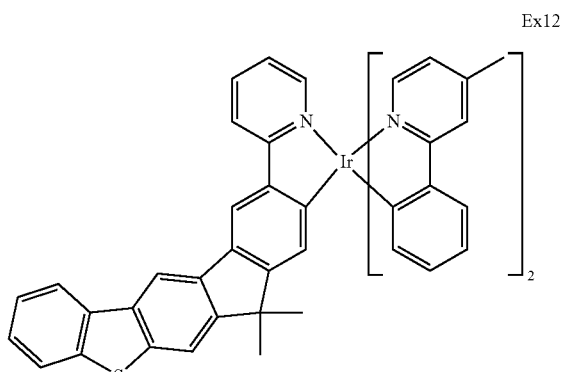
Ex13
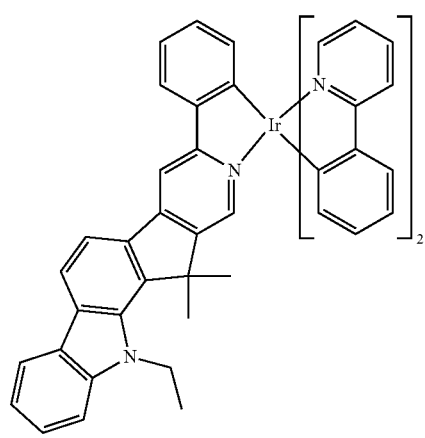
-continued
Ex14
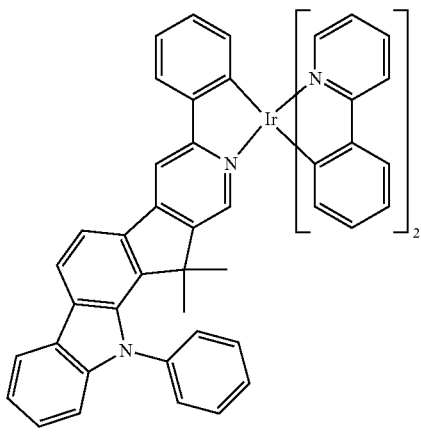
Ex15
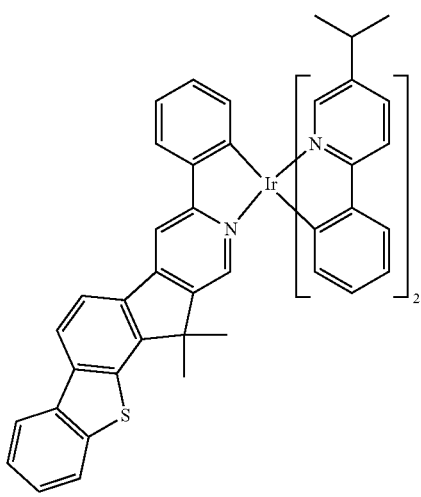
Ex16
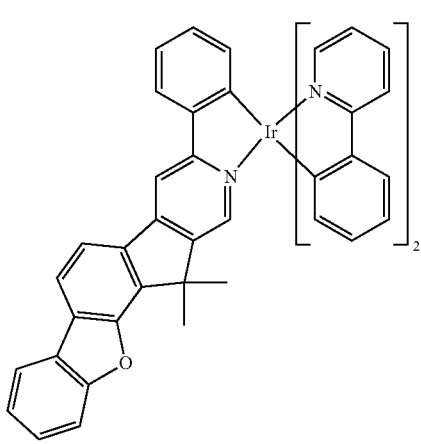

-continued
Ex17
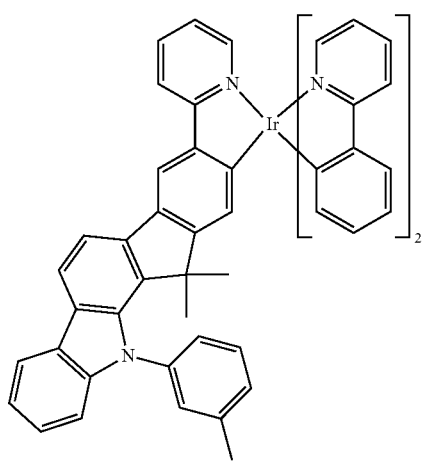
Ex18
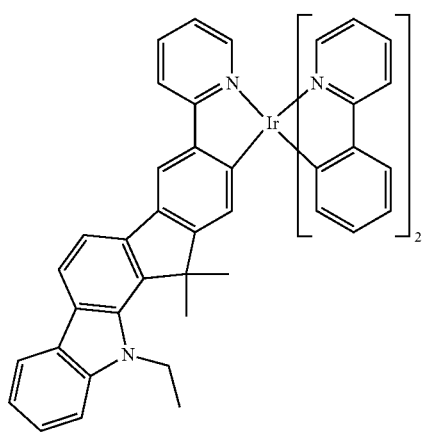
Ex19
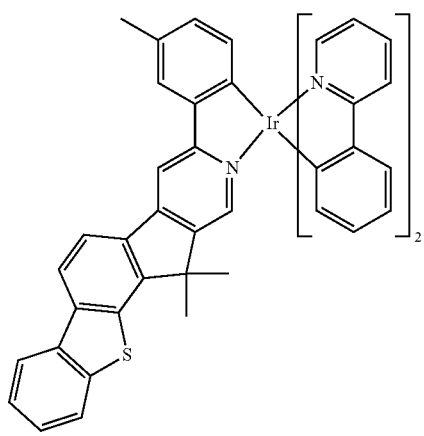
-continued
Ex20
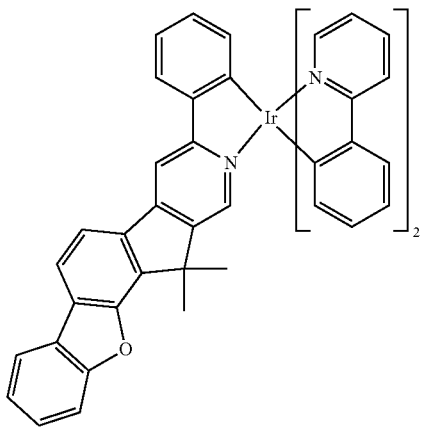
Ex21
Ex22

Ex23
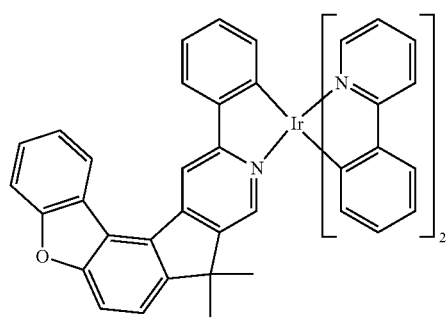
Ex24
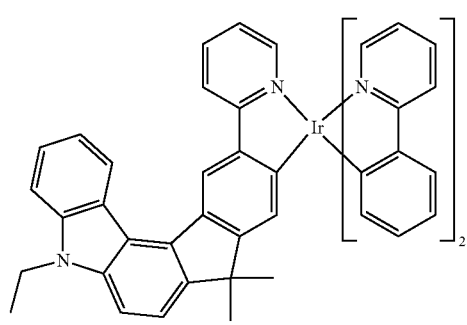
Ex25
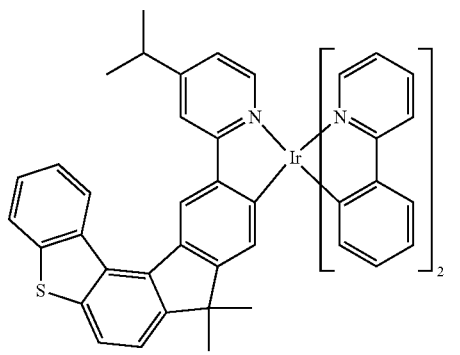
and
Ex26
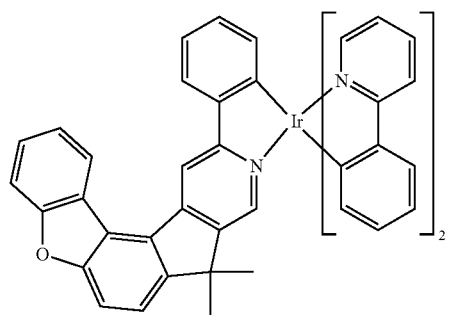
.
* * * * *